(12) United States Patent
Vogt et al.

(10) Patent No.: US 6,274,570 B1
(45) Date of Patent: Aug. 14, 2001

(54) PESTICIDAL COMPOSITIONS

(75) Inventors: Manfred Vogt, Bad Säckingen (DE); William Baettig, Pratteln (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 09/202,885

(22) PCT Filed: Jun. 19, 1997

(86) PCT No.: PCT/EP97/03193

§ 371 Date: Dec. 22, 1998

§ 102(e) Date: Dec. 22, 1998

(87) PCT Pub. No.: WO98/00008

PCT Pub. Date: Jan. 8, 1998

(30) Foreign Application Priority Data

Jun. 28, 1996 (EP) ................................................ 96810432

(51) Int. Cl.[7] ........................ A01N 57/00; A01N 25/00; A01N 31/00; A01N 33/00; A01N 35/00; A01N 37/00; A01N 53/00

(52) U.S. Cl. ........................ 514/89; 424/405; 504/116.1; 514/119; 514/144; 514/249; 514/277; 514/315; 514/383; 514/463; 514/471; 514/530; 514/531; 514/534; 514/538; 514/539; 514/540; 514/613; 514/640; 514/645; 514/647; 514/658; 514/691; 514/716; 514/717; 514/718; 514/721; 514/729; 514/730; 514/769; 514/770; 514/772; 514/774; 514/778; 514/781; 514/783; 514/784; 514/785; 514/937; 514/944; 514/975

(58) Field of Search .................................... 514/521, 522, 514/785, 89, 119, 144, 249, 277, 315, 383, 463, 471, 530, 531, 534, 538, 539, 540, 613, 640, 645, 647, 658, 691, 716, 717, 718, 721, 729, 730, 769, 770, 772, 774, 778, 781, 783, 784, 937, 944, 975; 424/405; 504/116.1

(56) References Cited

U.S. PATENT DOCUMENTS

| | | | |
|---|---|---|---|
| 4,175,094 | * 11/1979 | Reinink et al. | 558/345 |
| 4,564,632 | * 1/1986 | Nonn et al. | 514/522 |
| 4,870,103 | 9/1989 | Roechling et al. | 514/521 |
| 4,973,352 | 11/1990 | Heinrich et al. | 504/131 |
| 5,078,782 | * 1/1992 | Nielsen et al. | 504/135 |
| 5,645,856 | * 7/1997 | Lacy et al. | 424/455 |
| 5,658,851 | * 8/1997 | Murphy et al. | 504/362 |
| 6,071,857 | * 6/2000 | Vogt et al. | 504/366 |

FOREIGN PATENT DOCUMENTS

| | | |
|---|---|---|
| 3624910 | 1/1988 | (DE) . |
| 3640267 | 6/1988 | (DE) . |
| 4239181 | 5/1994 | (DE) . |
| 299961 | 1/1989 | (EP) . |
| 330904 | 9/1989 | (EP) . |
| 400585 | 12/1990 | (EP) . |
| WO 87/05778 | 10/1987 | (WO) . |
| WO-92/09195-A1 | * 6/1992 | (WO) . |
| WO-92/09197-A1 | * 6/1992 | (WO) . |
| 90/4202 | 6/1990 | (ZA) . |

OTHER PUBLICATIONS

Derwent Abstract 88–155852 (of DE 3640267) (1988).
Derwent Abstract 94–152415 (of DE 4239181) (1994).
Chemical Abstract 118:163258 (1993).
Derwent Abstract 87–291531 ( of WO 87/05778) (1987).
Chemical Abstract 118:118968 (1993).

* cited by examiner

Primary Examiner—Jose' G. Dees
Assistant Examiner—Frank Choi
(74) Attorney, Agent, or Firm—William A. Teoli, Jr.

(57) ABSTRACT

A liquid pesticidal composition, which is substantially free of water, comprising a hydrophobic pesticide or mixture of pesticides dissolved in an organic solvent and comprising as surfactants (a) a castor oil ethoxylate having 30–50 mol ethoxylate, (b) a branched $C_8$–$C_{18}$ alcohol ethoxylate having 5–10 mol ethoxylate, and (c) a tristyrenephenol-ethoxylate having 8–30 mol ethoxylate, or its phosphate or salt thereof. The compositions also include gels having a viscosity of 500 to 20,000 mPas and comprising additionally a gelling agent.

40 Claims, No Drawings

PESTICIDAL COMPOSITIONS

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

BACKGROUND OF THE INVENTION

1. Field of the Invention

The present invention relates to storage stable, liquid, pesticidal compositions, the preparation of such compositions and a method of using such compositions to combat pests or as plant growth regulators.

2. Description of the Related Art

Alkylphenol ethoxylates, for example nonylphenol ethoxylates, and alkylbenzene sulfonates and its salts, for example dodecylbenzene sulfonate calcium salt, are commonly used and well known surfactants in water-emulsifiable pesticidal compositions. Some of these surfactants are not entirely satisfactory; in particular with respect to their ecological and toxicological properties. There is still a need for further water-emulsifiable or water soluble, liquid, homogeneous pesticidal compositions which are storage stable, ecological and toxicological favorable and which have good pesticidal efficacy.

Fatty alcohol ethoxylates, e.g. $C_{10}$–$C_{14}$ alcohol ethoxylates (EP-A-400,585) and tristyrenephenol-ethoxylates (EP-A-102,003) have been proposed, both in combination with alkylbenzene sulfonates, as surfactants in water-emulsifiable pesticidal compositions. Combinations of castor oil ethoxylate, fatty alcohol ethoxylate, (e.g. tridecanol ethoxylate), tristyrene phenyl ethoxylate and alkylbenzene sulfonate have been disclosed as surfactants in aqueous microemulsions (DE 36 24 910).

BRIEF SUMMARY OF THE INVENTION

It has been found that the combination of a castor oil ethoxylate with a branched $C_8$–$C_{18}$ alcohol ethoxylate and a tristyrenephenol-ethoxylate is a very advantageous surfactant system for water-emulsifiable or water-soluble pesticidal compositions; the novel compositions are storage stable, easy to apply, ecological and toxicological favorable and have good pesticidal efficacy.

BRIEF DESCRIPTION OF THE SEVERAL VIEWS OF THE DRAWINGS

Not applicable.

DETAILED DESCRIPTION OF THE INVENTION

Accordingly, the present invention provides a water-emulsifiable or water-soluble, storage stable, liquid, pesticidal composition, which is substantially free of water, comprising a hydrophobic pesticide or mixture of pesticides dissolved in an organic solvent and comprising as surfactants (a) a castor oil ethoxylate having 30–50 mol ethoxylate, (b) a branched $C_8$–$C_{18}$ alcohol ethoxylate having 5–10 mol ethoxylate, and (c) a tristyrenephenol-ethoxylate having 8–30 mol ethoxylate, or its phosphate or salt thereof.

Suitable salts with bases are, for example, metal salts, such as alkali metal or alkaline earth metal salts, for example sodium, potassium calcium or magnesium salts, or salts with ammonia or an organic amine, such as morpholine, piperidine, pyrrolidine, a mono-, di- or tri-lower alkylamine, for example ethyl-, diethyl-, triethyl- or dimethyl-propylamine, or a mono-, di- or tri-hydroxy-lower alkylamine, for example mono-, di- or tri-ethanolamine.

The compositions also include gels having a viscosity of 500 to 20,000 mPas and comprising additionally a gelling agent.

The compositions according to the invention are stable for at least 12 months at 25° C. They are very well miscible, with water, even at higher concentrations.

The surfactants mentioned above can be prepared by methods known per se; they are also commercially available. Preferred are surfactants, wherein (a) the castor oil ethoxylate has 36–40 mol, preferably 36–37 mol ethoxylate;

(b) the branched $C_8$–$C_{18}$ alcohol ethoxylate is isotridecanol ethoxylate having 5–10 mol, preferably 6–8 mol ethoxylate;

(c) the tristyrenephenol-ethoxylate has 16–18 mol ethoxylate.

It may be advantageous to add additionally an alkylbenzene sulfonate or its salt, preferably dodecylbenzene sulfonate calcium salt in an amount of 1 to 10%, preferably 2 to 4% by weight in relation to the volume of the composition.

The composition of the invention is substantially free of water, i.e. the amount of water is less that 0.5%. Some commercially available materials may contain a small amount of water, which, when more than about 0.1% can be removed for example in a separator.

In another aspect of the invention the composition is a gel with a viscosity of 500–20,000 mPas; preferably 800 to 10,000 mPas and particularly 1000–5000 mPas. The viscosity of the composition can be measured using for example a BROOKFIELD viscosimeter with spindles 1 to 3 at 30 rpm. In this case the composition additionally has to contain a gelling agent, for example oxypropylated cellulose, precipitated or fused silica (hydrophobisized or non-hydrophobisized), gelatine, polysaccharides, tetramethyl decyne diol, ethoxylated dialkyl phenol, methylated clay, propylene carbonate, hydrogenated castor oil, ethoxylated vegetable oil, sodium benzoate and hexanediol. Preferred gelling agent is oxypropylated cellulose. Gels are particularly suitable for pesticides packed into water soluble bags or sachets, which quickly dissolve when put into the water.

The organic solvents wherein the pesticide has to be dissolved may be water-immiscible or water miscible or a mixture thereof. Suitable water-immiscible solvents in which the pesticides may be dissolved are aliphatic and aromatic hydrocarbons such as hexane, cyclohexane, benzene, toluene, xylene, mineral oil or kerosene, mixtures or substituted naphthalenes, mixtures of mono- and poly-alkylated aromatics commercially available under the registered trademarks SOLVESSO and SHELLSOL and PETROL SPEZIAL, halogenated hydrocarbons such as methylene chloride, chloroform and o-dichlorobenzene; phthalates, such as dibutyl phthalate or dioctyl phthalate; ethers and esters, such as ethylene glycol monomethyl or monoethyl ether, fatty acid esters; lactones such as butyrolactone, ketones, such as cyclohexanone; plant oils such as castor oil, soybean oil, cottonseed oil and possible methyl esters thereof; as well as epoxidised coconut oil or soybean oil. Preferred water-immiscible solvents are aliphatic and aromatic hydrocarbons, fatty acid esters (e.g. WITCONOL 2309), dipropyleneglycol monomethylether (e.g. DOWANOL DPM) and castor oil. Suitable water-miscible solvents in which the pesticides may be dissolved are alcohols and glycols, such as ethanol, ethylene glycol, strongly polar solvents, such as N-methyl-2-pyrrolidone, tetramethylurea, gamma-butyrolactone, dimethyl sulfoxide, N,N-dimethylacetamide and dimethylformamide; preferred are N-methyl-2-pyrrolidone and gamma-butyrolacone.

Suitable pesticides are those which are substantially insoluble in water (hydrophobic), but soluble in the organic solvent. The term pesticide is understood to encompass herbicides, insecticides, acaricides, nematicides, ectoparasiticides, fungicides and plant growth regulators. With respect to their chemical constitution, these pesticides may belong to a very wide range of compound classes. Examples of compound classes to which the suitable pesticide may belong are: acylalanines, haloacetanilides, triazole derivatives, phosphoric acid esters, pyrethroids, benzilic acid esters, polycyclic halogenated hydrocarbons, diphenyl ether derivates, formamidines, strobilurines, aryloxyphenoxy-alkanoic acid derivatives. Examples of suitable individual compounds of the above mentioned compound classes are listed below. Where known, the common name is used to designate the individual compounds (q.v. the Pesticide Manual, 10th edition, 1994,British Crop Protection Council).

Haloacetanilides: Dimethachlor, Metolachlor, Pretilachlor, 2-chloro-N-(1-methyl-2-methoxyethyl) -acet-2,6-xylidide, Alachlor, Butachlor, Propachlor, Dimethenamid.

Diphenyl ether derivates: Bifenox, 4-(4-Pentyn-1-yloxy) diphenylether, Acifluorfen, Oxyfluorfen, Fluoroglycofen-ethyl, Fomesafen, cis-trans-(±)2-ethyl-5-(4-phenoxy-phenoxymethyl)-1,3-dioxolane ("diofenolan").

Phenoxypropionic acid derivatives: Fluazifop-butyl, Haloxyfop-methyl, Haloxyfop-(2-ethoxyethyl), Fluorotopic, Fenoxapropethyl, Quizalofop-ethyl, Propaquizafop, Diclofop-methyl.

Acylalanines: Furalaxyl, Metalaxyl, R-Metalaxyl, Benzoyl-prop ethyl, Benalaxyl, Oxadixyl, Flamprop methyl.

Triazole derivatives: Difenoconazole, Etaconazol, Propiconazole, Penconazole, Triadimefon, Epoxiconazole, Tebuconazole, Bromuconazole, Fenbuconazole, Cyproconazole.

Phosphoric acid esters: Piperophos, Anilofos, Butamifos, Azamethiphos, Chlorfenvinphos, Dichlorvos, Diazinon, Methidathion, Azinphos ethyl, Azinphos methyl, Chlorpyrifos, Chlorthiofos, Crotoxyphos, Cyanophos, Demeton, Dialifos, Dimethoate, Disulfoton, Etrimfos, Famphur, Flusulfothion, Fluthion, Fonofos, Formothion, Heptenophos, Isofenphos, Isoxathion, Malathion, Mephospholan, Mevinphos, Naled, Oxydemeton methyl, Oxydeprofos, Parathion, Phoxim, Pyrimiphos methyl, Profenofos, Propaphos, Propetamphos, Prothiophos, Quinalphos, Sulprofos, Phemephos, Terbufos, Triazophos, Trichloronate, Fenamipos, Isazophos, s-benzyl-o,o-diisopropylphosphorothioate, Edinphos, Pyrazophos.

Pyrethroids: Allethrin, Bioallethrin, Bioresmethrin, Cyhalotrin, Cypermethrin, α-Cypermethrin, φ-Cypermethrin, Deltamethrin, Fenpropathrin, Fenvalerate, s-Fenvalerate, Flucythrinate, Fluvalinate, Permethrin, Pyrethrine, Resmethrin, Tetramethrin, Tralomethrin, Ethophenprox, Cyfluthrin, Cycloprothrin, Tefluthrin, Flufenprox, Silafluofen, Bifenthrin, Fenfluthrin, Bromfenprox.

Benzilic acid esters: Brompropylate, Chlorbenzylate, Chlorpropylate.

Polycyclic halogenated hydrocarbons: Aldrin, Endosulfan.

Strobilurines: Kresoxim-methyl, Azoxystrobin (BAS 490F), Methoxyimino-{2-[1-(3-trifluoromethyl-phenyl) -ethylideneaminooxymethyl]-phenyl}-acetic acid methyl ester.

Miscellaneous: Tridemorph, Bromoxynil, Carboxin, Prochloraz, Propargite, Dicamba, Fenpiclonil, Fenpropimorph, Fenpropidin, Fludioxonil, Pymetrozine, Pyrifenox, Pyriproxyfen, Trinexapac-ethyl, Fluazinam.

Preferred pesticides are herbicides, as Propaquizafop, Piperophos and Propanil;

fungicides, as Methoxyimino-{2-[1-(3-trifluoromethyl-phenyl)-ethylideneaminooxymethyl]-phenyl}-acetic acid methyl ester, Propiconazole, Cyproconazole, Fluazinam, Metalaxyl or R-Metalaxyl (enantiomer of Metalaxyl), or a mixture thereof;

plant growth regulators, as Trinexapac-ethyl.

Suitable concentrations in relation to the composition are (% weight per volume of the total composition; 1000 g per liter correspond to 100%)

of the hydrophobic pesticide or mixture of pesticides: 1 to 99%, preferably 10 to 90% and 10 to 60%;

of the organic solvent: 1 to 96%, preferably 10 to 80% and 20 to 70%;

of the surfactants: 3 to 80%, preferably 5 to 40% and 10 to 30%; wherein of surfactant (a): 1 to 30%, preferably 2 to 20%, surfactant (b): 1 to 40%, preferably 2 to 20%, surfactant (c): 1 to 20%, preferably 2 to 15%;

of the gelling agent: 0.1 to 10% preferably 0.5 to 5%.

It may be advantageous to combine the pesticide or mixture of pesticides with a safener.

Another object of the invention is a process for preparing a liquid pesticidal composition as herein described, by intimateley mixing, optionally by warming, until a homogeneous phase is achieved.

In another aspect of the invention the composition is an aqueous spray mixture.

Before the application, the composition of the invention may be diluted with water by simple mixing at ambient temperature in order to prepare a 'ready to use' mixture for spraying.

This spray mixture may be an aqueous emulsion or a solution or a suspension, depending on the kind of composition. The resulting spray mixtures are stable, i.e. they remain as a homogeneously emulsified phase, as a solution or as a homogeneously distributed suspension on standing without agitation for at least one hour to 12 hours or even more. Preferred concentrations of the spray mixture are 0.1 to 5%, more preferred 0.5 to 2% pesticide in relation to the spray mixture.

Further aspects of the invention include a method of preventing or combatting infestation of plants or animals by pests and regulating plant growth by diluting the composition with water and applying a pesticidally effective amount to the plant, animal or locus as desired.

PREPARATION EXAMPLES

The following Examples illustrate the invention in more detail. The registered trademarks and other designations denote the following products:

(a) EMULSOGEN EL® castor oil-36–37 EO
(b) GENAPOL X-080® (HOECHST) Isotridecanol-8 EO
GENAPOL X-060® (HOECHST) Isotridecanol-6 EO
(c) SOPROPHOR BSU® (RHÒNE-P) Tristyrenephenole-16 EO SOPROPHOR 3D33® (RHÒNE-P) Tristyrenephenol-poly-EO-phosphate
WITCONOL 2309® Fatty acid methylester
PETROL SPEZIAL 200® Mixture of aromatic hydrocarbons
KLUCEL M® Oxypropylated cellulose (gelling agent)
DOWANOL DPM® Dipropyleneglycol monomethylether (mixture of isomers)
EO=ethyleneoxide
PO=propyleneoxide
% in weight per volume of the total composition (i.e.1000 g·per liter correspond to 100%) The components are intimately mixed, optionally by warming, until a homogeneous phase is achieved.

| % | component | type |
|---|---|---|
| | Example 1 | |
| 100 | Propaguizofop | herbicide |
| 5.0 | EMULSOGEN EL ® | surfactant (a) |
| 30.0 | GENAPOL X-060 ® | surfactant (b) |
| 5.0 | SOPROPHOR BSU ® | surfactant (c) |
| 10.0 | 1-Methyl-2-pyrrolidone | solvent |
| 40.0 | PETROL SPEZIAL 200 | solvent |
| | Example 2 | |
| 14.5 | Piperophos | herbicide |
| 25.0 | Propanil | herbicide |
| 4.0 | EMULSOGEN EL ® | surfactant (a) |
| 12.0 | GENAPOL X-060 ® | surfactant (b) |
| 4.0 | SOPROPHOR BSU ® | surfactant (c) |
| 47.0 | Dipropyleneglycol monomethyl ether | solvent |
| | Example 3 | |
| 9.3 | R-Metalaxyl | fungicide |
| 4.0 | EMULSOGEN EL ® | surfactant (a) |
| 12.0 | GENAPOL X-060 ® | surfactant (b) |
| 4.0 | SOPROPHOR BSU ® | surfactant (c) |
| 5.0 | Gamma-Butyrolactone | solvent |
| 27.0 | Fatty acid methyl ester Me C 6–10 | solvent |
| | Example 4 | |
| 20.0 | R-Metalaxyl | fungicide |
| 30.0 g | Fluazinam | fungicide |
| 6.0 | EMULSOGEN EL ® | surfactant (a) |
| 6.0 | GENAPOL X-060 ® | surfactant (b) |
| 6.0 | SOPROPHOR BSU ® | surfactant (c) |
| 30.0 | Gamma-Butyrolactone | solvent |
| rest | Aromatic Solvent 230 | solvent |
| | Example 5 | |
| 10.0 | R-Metalaxyl | fungicide |
| 20.0 g | Fluazinam | fungicide |
| 6.0 | EMULSOGEN EL ® | surfactant (a) |
| 6.0 | GENAPOL X-060 ® | surfactant (b) |
| 6.0 | SOPROPHOR BSU ® | surfactant (c) |
| 30.0 | Gamma-Butyrolactone | solvent |
| rest | Aromatic Solvent 230 | solvent |
| | Example 6 | |
| 20.0 | R-Metalaxyl | fungicide |
| 40.0 g | Fluazinam | fungicide |
| 3.0 | EMULSOGEN EL ® | surfactant (a) |
| 3.0 | GENAPOL X-060 ® | surfactant (b) |
| 3.0 | SOPROPHOR BSU ® | surfactant (c) |
| 2.0 | dodecyl benzene sulfonate Ca-salt | surfactant |
| 15.0 | Gamma-Butyrolactone | solvent |
| rest | Aromatic Solvent 230 | solvent |

| % | component | type |
|---|---|---|
| | Example 7 | |
| 26.3 | Trinexapac-ethyl | plant growth regulator |
| 11.4 | EMULSOGEN EL ® | surfactant (a) |
| 7.1 | GENAPOL X-060 ® | surfactant (b) |
| 10.0 | SOPROPHOR BSU ® | surfactant (c) |
| 45.2 | WITCONOL 2309 | sovent |
| | Example 8 (Gel) | |
| 26 | Trinexapac-ethyl | plant growth regulator |
| 11.4 | EMULSOGEN EL ® | surfactant (a) |
| 7.1 | GENAPOL X-060 ® | surfactant (b) |
| 10.0 | SOPROPHOR BSU ® | surfactant (c) |
| 1.0 | Klucel M ® | gelling agent |
| rest | DOWANOL DPM ® | solvent |

Viscosity: ca. 2900 mPas (Spindle 3/30 rpm)

All the compositions according to the examples are stable for at least 12 months at 25° C.

After diluting with water the compositions form an emulsion or, depending on the pesticide, solvent and concentration, a clear solution. Both the emulsions and solutions are stable without agitation for at least one to 12 hours or even more.

What is claimed is:

1. A liquid pesticidal composition comprising a hydrophobic pesticide or mixture of pesticides dissolved in an organic solvent and comprising as surfactants
   (a) a castor oil ethoxylate having 30–50 mol ethoxylate
   (b) a branched $C_8$–$C_{18}$ alcohol ethoxylate having 5–10 mol ethoxylate, and
   (c) a tristyrenephenol-ethoxylate having 8–30 mol ethoxylate, or its phosphate or salt thereof
said composition being substantially free of water, wherein said organic solvent is selected from the group consisting of a water-miscible solvent, a water-immiscible solvent, and mixtures thereof, wherein said water-immisible solvent is selected from aliphatic and aromatic hydrocarbons, halogenated hydrocarbons, phthalates, ethers and esters, fatty acid esters, lactones, ketones, plant oils, methyl esters of said plant oils, epoxidized coconut oil, epoxidized soybean oil and mixtures thereof; and wherein said water-miscible solvent is selected from the group consisting of alcohols, glycols, N-methyl-2-pyrrolidone, tetramethylurea, gamma-butyrolactone, dimethylsulfoxide, N,N-dimethylacetamide, N,N-dimethylformamide, and mixtures thereof;
whereby said composition is capable of being stably stored for a period of at least one year at 25° C.

2. The composition according to claim 1, wherein the castor oil ethoxylate (a) has 36–40 mol ethoxylate.

3. The composition of claim 2 wherein the castor oil ethoxylate (a) has 36–37 mol ethoxylate.

4. The composition according to claim 1, wherein the branched $C_8$–$C_{18}$ alcohol ethoxylate (b) is isotridecanol ethoxylate having 5–10 mol ethoxylate.

5. The composition of claim 4 wherein the branched $C_8$–$C_{18}$ alcohol ethoxylate (b) is isotridecanol ethoxylate having 6–8 mol ethoxylate.

6. The composition according to claim 1, wherein the tristyrenephenol-ethoxylate (c) has 16–18 mol ethoxylate.

7. The composition according to claim 1 which is a gel having a viscosity of 500 to 20,000 mPas and comprising additionally a gelling agent.

8. The composition according to claim 7, wherein the concentration of the gelling agent is 0.1 to 10% by weight in relation to the volume of the composition.

9. The composition of claim 8 wherein said gelling agent is present in said composition at a concentration of 0.5 to 5% in relation to the volume of the composition.

10. The composition according to claim 7 having a viscosity of 800 to 10,000 mPas.

11. The composition of claim 10 having a viscosity of 1000–5000 mPas.

12. The composition according to claim 7 wherein the gelling agent is selected from the group consisting of oxypropylated cellulose, precipitated or fused silica (hydrophobisized or non-hydrophobiszed), gelatine, polysaccharides, tetramethyl decyne diol, ethoxylated dialkyl phenol, methylated clay, propylene carbonate, hydrogenated castor oil, ethoxylated vegetable oil, sodium benzoate and hexanediol.

13. The composition according to claim 12, wherein the gelling agent is oxypropylated cellulose.

14. The composition according to claim 1, wherein the organic solvent is water-immiscible.

15. The composition according to claim 1, wherein the organic solvent is water-miscible.

16. The composition according to claim 1, wherein the pesticide is a herbicide.

17. The composition of claim 16 wherein said pesticide is a herbicide and is selected from the group consisting of Propaquizafop, Piperaphos, and Propanil.

18. The composition according to claim 1, wherein the pesticide is a fungicide.

19. The composition of claim 18 wherein said pesticide is a fungicide and is selected from the group consisting of methoxyimino-{2-[1-(3-trifluoromethyl-phenyl) ethylideneaminooxymethyl]-phenyl} acetic acid methyl ester, Propiconazole, Cyproconazole, Fluazinam, Metalaxyl or R-Metalaxyl, and mixtures thereof.

20. The composition according to claim 1, wherein the pesticide is a plant growth regulator.

21. The composition of claim 20 wherein said pesticide is Trinexapac-ethyl.

22. The composition according to claim 1, wherein the concentration of the pesticide or mixture of pesticides is 1 to 99% by weight in relation to the volume of the composition.

23. The composition according to claim 22, wherein the concentration of the pesticide or mixture of pesticides is 10 to 90% in relation to the volume of the composition.

24. The composition of claim 23 wherein said pesticide is present in said composition at a concentration of 10 to 60% in relation to the volume of the composition.

25. The composition according to claim 1, wherein the concentration of the organic solvent is 1 to 96% by weight in relation to the volume of the composition.

26. The composition according to claim 25, wherein the concentration of the organic solvent is 10 to 80% by weight in relation to the volume of the composition.

27. The composition of claim 26 wherein said organic solvent is present in said composition at a concentration of 20 to 70% in relation to the volume of the composition.

28. The composition according to claim 1, wherein the concentration of the surfactants is 3 to 80% by weight in relation to the volume of the composition.

29. The composition according to claim 28, wherein the concentration of the surfactants is 5 to 40% by weight in relation to the volume of the composition.

30. The composition of claim 29 wherein said surfactants are present in said composition at a concentration of 10 to 30% in relation to the volume of the composition.

31. The composition according to claim 1, further comprising an alkylbenzene sulfonate or a salt thereof.

32. The composition of claim 31 wherein said alkylbenzene sulfonate or its salt is dodecylbenzene sulfonate calcium salt.

33. The composition of claim 1, wherein the organic solvent is selected from aliphatic and aromatic hydrocarbons, fatty acid esters and dipropyleneglycol monomethylether.

34. The composition of claim 1, wherein the organic solvent is selected from the group consisting of N-methyl-2-pyrrolidone and gamma-butyrolactone or a mixture thereof.

35. A process for preparing a liquid pesticidal composition according to claim 1 by intimately mixing, optionally by warming, said pesticide or pesticides, said organic solvent, and said surfactants (a), (b), and (c) until a homogeneous phase is achieved.

36. An aqueous microemulsion or solution prepared by mixing the composition according to claim 1 with water.

37. A method of preventing or combatting infestation of plants or animals by pests and regulating plant growth by diluting the composition according to claim 1 with water and applying a pesticidally effective amount to the plant, animal or locus.

38. A liquid pesticidal composition comprising a hydrophobic pesticide or mixture of pesticides dissolved in an organic solvent and comprising a mixture of surfactants consisting essentially of
  (a) a castor oil ethoxylate having 30–50 mol ethoxylate;
  (b) a branched $C_8$–$C_{18}$ alcohol ethoxylate having 5–10 mol ethoxylate;
  (c) a tristyrenephenol-ethoxylate having 8–30 mol ethoxylate, or its phosphate or salt thereof, and
  (d) optionally an alkylbenzenesulfonate or a salt thereof;
said composition being substantially free of water, whereby said composition is capable of being stably stored for a period of at least one year at 25° C.

39. An aqueous microemulsion or solution prepared by mixing the composition according to claim 38 with water.

40. A method of preventing or combatting infestation of plants or animals by pests and regulating plant growth by diluting the composition according to claim 38 with water and applying a pesticidally effective amount to the plant, animal or locus.

* * * * *